United States Patent
Yang

(10) Patent No.: US 10,688,241 B2
(45) Date of Patent: Jun. 23, 2020

(54) MULTI-MODE POWER SUPPLY SYSTEM FOR A PORTABLE INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Zhangjian Hi-Tech Park, Pudong New Area, Shanghai (CN)

( * ) Notice: Subject to any disclaimer, the term of this patent is extended or adjusted under 35 U.S.C. 154(b) by 62 days.

(21) Appl. No.: 16/094,719

(22) PCT Filed: Apr. 18, 2016

(86) PCT No.: PCT/CN2016/079575
§ 371 (c)(1),
(2) Date: Oct. 18, 2018

(87) PCT Pub. No.: WO2017/181325
PCT Pub. Date: Oct. 26, 2017

(65) Prior Publication Data
US 2019/0117882 A1      Apr. 25, 2019

(51) Int. Cl.
*H02J 7/00*      (2006.01)
*A61M 5/142*    (2006.01)
(Continued)

(52) U.S. Cl.
CPC ........ *A61M 5/14244* (2013.01); *A61M 5/142* (2013.01); *H02J 7/342* (2020.01);
(Continued)

(58) Field of Classification Search
CPC .... H02J 7/342; A61M 5/14244; A61M 5/142; A61M 5/14; A61M 2205/16; A61M 2205/8206
(Continued)

(56) References Cited

U.S. PATENT DOCUMENTS 6,063,058 A * 5/2000 Sakamoto ............. A61M 5/152
                                                            128/DIG. 12
6,530,901 B1 * 3/2003 Tsukada ................ A61M 5/152
                                                                604/132
(Continued)

FOREIGN PATENT DOCUMENTS

CN         205095137 U      3/2016

*Primary Examiner* — Phallaka Kik
(74) *Attorney, Agent, or Firm* — Global IP Services; Tianhua Gu

(57) ABSTRACT

A multi-mode power supply system for a portable infusion device is provided, comprising a Battery I and an Battery II, the Battery I constantly charges the Battery II constituting a charging circuit, which adopts one of multiple charging modes including a basal-rate slow charging mode, a bolus-dose fast charging mode and a background charging mode depending on different drug infusion conditions; the Battery I powers the control unit independently, and the Battery II powers the driving unit independently; a unidirectional conduction circuit, a monitoring circuit and a detecting circuit are further comprised to ensure the normal operation of the power supply system under various circumstances. Any two of the Battery I, the Battery II, the driving unit and the control unit can be located in one housing, and the other two in the other housing; regardless of any particular combination, the coupling of the Battery I with the control unit and the Battery II with the driving unit are both implemented directly by a connecting element or connecting elements. This implementation of power supply meets both needs of basic functions and high power functions of the system with stability and efficiency.

15 Claims, 4 Drawing Sheets

(51) Int. Cl.
*A61M 5/14* (2006.01)
*H02J 7/34* (2006.01)

(52) U.S. Cl.
CPC ............ *A61M 5/14* (2013.01); *A61M 2205/16* (2013.01); *A61M 2205/8206* (2013.01)

(58) Field of Classification Search
USPC .................. 320/114, 110, 112, 124, 125, 167
See application file for complete search history.

(56) References Cited

U.S. PATENT DOCUMENTS

| | | | |
|---|---|---|---|
| 9,377,513 B2 * | 6/2016 | Lindegger | A61M 5/14 |
| 2008/0208114 A1 * | 8/2008 | Landau | A61M 5/2053 |
| | | | 604/68 |
| 2008/0243079 A1 | 10/2008 | Wooley et al. | |
| 2011/0060318 A1 | 3/2011 | Frey | |
| 2016/0144105 A1 * | 5/2016 | Hooven | A61M 5/152 |
| | | | 604/132 |

* cited by examiner

MULTI-MODE POWER SUPPLY SYSTEM FOR A PORTABLE INFUSION DEVICE

TECHNICAL FIELD

The present invention generally relates to the field of medical appliance, more particularly, to a multi-mode power supply system for a portable infusion device.

BACKGROUND OF THE INVENTION

Currently, a portable device in the market is usually powered by either an alkaline battery, a lithium-ion battery or a NiMH battery. One drawback of battery operated devices is the inability to utilize all of the energy stored in the battery due to the natural voltage decay associated with energy depletion. This particular problem is most prevalent with alkaline batteries, which tend to suffer a drop in voltage after a relatively short period of operating time even though an adequate amount of stored energy remains. Compared with alkaline batteries, Lithium-ion and nickel-metal hydride batteries tend to maintain a more stable voltage over time, which generally allows for a higher percentage of the stored energy to be utilized. Although lithium and NiMH batteries maintain a very stable voltage over time, they suffer from a sharp voltage drop at the end of life. Predicting when this drop will occur is very difficult and often requires a great deal of testing and characterization to send a warning to a user before the actual end of the battery life.

To solve the problems identified above, some companies proposed new approaches to the power supply of portable electronic devices, as a two-battery power supply system with three power phases disclosed in the publication of US2015263561A1 by Medtronic Minimed, in which one rechargeable battery can be recharged by a replaceable battery, and the two batteries provide energy for the basic functions and/or high voltage functions respectively under different power phases; another instance is a power supply system and method using two batteries for an analyte measurement device disclosed in the publication of US20140059360A1 by Lifescan Scotland Ltd, making the working life of the device twice as long as compared to the traditional device relying on a single battery as the only power supply. Both publications involve power supply with two batteries as well as assemblies and methods for detecting the remaining capacity of the batteries, however, neither involves different charging modes depending on different operating modes of the device to meet different operating requirements, nor of them discussed the layout of the battery and the assemblies to be powered in the device, so as to say, the subject of minimizing the cost and maximizing the efficiency of the assemblies by the optimal permutations under the condition of the device being partly disposable is not considered.

A supercapacitor is a high-capacity electrochemical capacitor with capacitance values much higher than other capacitors that bridge the gap between electrolytic capacitors and rechargeable batteries whose energy storage process is a physical process with advantages of high power density, short charging time, long life, good temperature characteristics, energy conservation and environmental friendliness. It can be charged to any potential within the range of the rated voltage, and can be discharged completely, at the same time, neither over charge nor over discharge puts a negative impact on its life. Energy pulses can be transmitted repeatedly by supercapacitors and the charging-discharging circle can be repeated hundreds of thousands times. If the high power density of the capacitor and the high energy storage of the battery can be combined together, a better power supply method for portable devices can be created.

SUMMARY OF THE INVENTION

Regarding the above-mentioned shortcomings of the prior art, the present invention provides a multi-mode power supply system for a portable infusion device, comprising:

a Battery I, a Battery II, the Battery I is coupled with the Battery II, the Battery I is further coupled with a control unit, the Battery II is further coupled with a driving unit;

wherein, the Battery I is able to constantly charge the Battery II constituting a charging circuit, configured to maintain the voltage of the Battery II at a certain level;

the Battery I powers the control unit independently constituting a power supply circuit A, configured to ensure the infusion control of the portable infusion device by the control unit;

the Battery II powers the driving unit independently constituting a power supply circuit B, configured to drive the drug infusion;

the power supply circuit A and the power supply circuit B are independent from each other;

the charging circuit adopts one of multiple charging modes depending on different drug infusion conditions;

Alternatively, the multiple charging modes comprise:

a basal-rate slow charging mode, a bolus-dose fast charging mode and a background charging mode;

Alternatively, further comprises a unidirectional conduction circuit, when the Battery I suddenly fails or is disconnected from the power supply circuit A, the multi-mode power supply system enters into a power failure protection mode, under which the Battery II powers the control unit via the unidirectional conduction circuit;

Alternatively, further comprises a monitoring circuit, the monitoring circuit is configured to monitor the voltage of the Battery II, controlling the Battery I to charge the Battery II when the voltage of the Battery II is below a predetermined amount, and suspending the charging when the voltage of the Battery II reaches another predetermined amount;

Alternatively, the Battery I is a button battery;

Alternatively, the Battery I is a wireless charging induction coil;

Alternatively, the Battery II is a supercapacitor;

Alternatively, the Battery II is a rechargeable battery;

Alternatively, the rechargeable battery is a lithium-ion battery or a NiMH battery.

Alternatively, further comprises a detecting circuit, the detecting circuit is monitoring the operating state of the driving unit in real time via detecting the voltage change of the Battery II caused by a single time infusion;

Alternatively, the Battery II powers the driving unit directly, configured to implement a variable voltage drive;

Alternatively, the Battery II powers the driving unit via a DC-DC converter, configured to implement a stable voltage drive;

Alternatively, the Battery II powers the driving unit via a LDO regulator, configured to implement a stable voltage drive;

Alternatively, further comprises a connecting element or connecting elements;

Alternatively, any two of the Battery I, the Battery II, the driving unit and the control unit are located in one housing, and the other two are located in the other housing, regardless of any particular combination of these four components in the two housings, the coupling of the Battery I with the control unit and the Battery II with the driving unit are both implemented directly by a connecting element or connecting elements;

Alternatively, the number of the connecting element/connecting elements can be one or more;

Alternatively, the portable infusion device is a patch pump.

Compared to prior arts, the multi-mode power supply system for a portable infusion device in the present invention has advantages in the following ways:

Firstly, there is only one mode regarding one battery charging another in the prior art, but with the multi-mode power supply system in the present invention, strategy adjustments of multi-mode charging can be made based on different infusion requirements, making the Battery I charge the Battery II in multiple modes, comprising: a basal-rate slow charging mode with a small current when the portable infusion device is operating under the basal-rate delivery mode, a bolus-dose fast charging mode with a high current when the portable infusion device is operating under the bolus-dose delivery mode, and a background charging mode with a micro current when there is no delivery taking place, to meet the requirements of multiple operating modes of the portable infusion device, which keeps the charging constant and more efficient, and extends the life of the Battery I at the same time. Secondly, any two of the Battery I, the Battery II, the driving unit and the control unit can be located in a same housing A, and the other two in the other housing B which can be separated from the before-mentioned housing A, and regardless of any particular combination of these four components in the two housings, the independent power supply of the Battery I for the control unit as well as the Battery II for the driving unit is predetermined, which can be realized by a single or multiple connecting elements directly, providing possibility of being partly-disposable for the portable infusion device. Thirdly, the Battery II of the multi-mode power supply system in the present invention can be a supercapacitor with advantages of high power density, short charging time, long life, good temperature characteristics, energy conservation and environmental friendliness, which brings more efficiency and stability to the power supply system.

DETAILED DESCRIPTION

To make the above-mentioned objects, features and advantages of the present invention more obvious and understandable, the embodiments of the present invention are described in the following through specific embodiments.

Figure 1:
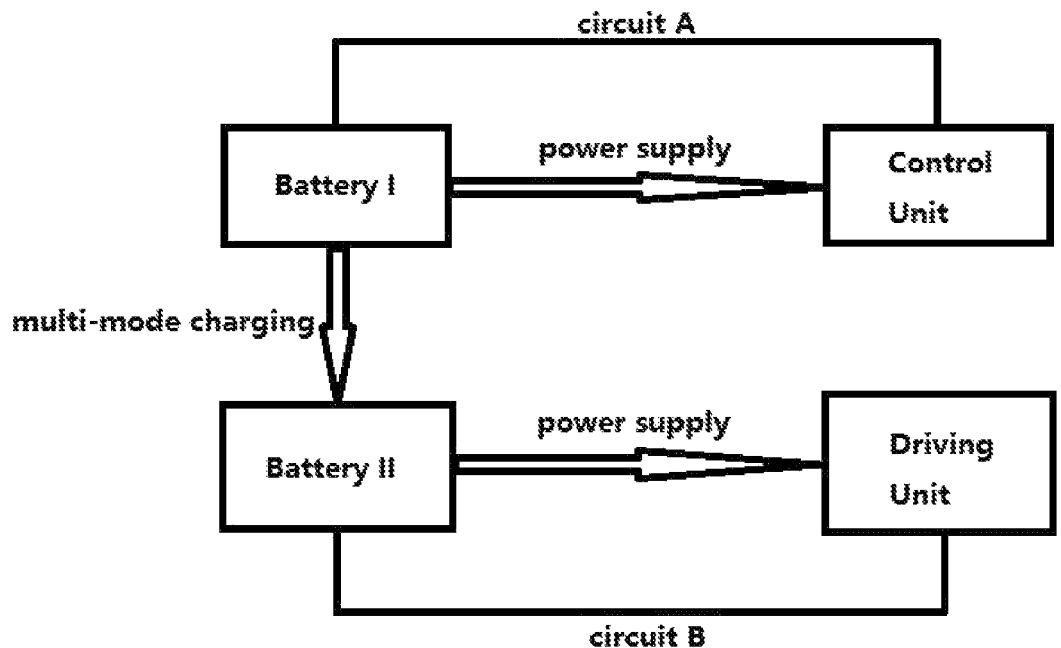
FIG. 1 illustrates a schematic of a multi-mode power supply system for a portable infusion device in the present invention.

Referring to FIG. 1, an exemplary embodiment of the multi-mode power supply system for a portable infusion device in the present invention is provided, comprising: a Battery I, a Battery II, the Battery I is able to constantly charge the Battery II constituting a charging circuit, configured to maintain the voltage of the Battery II at a certain level; the charging circuit adopts one of multiple charging modes depending on different drug infusion conditions, comprising: a basal-rate slow charging mode with a small current when the portable infusion device is operating in the basal-rate delivery mode, a bolus-dose fast charging mode with a high current when the portable infusion device is operating under the bolus-dose delivery mode, and a background charging mode with a micro current when there is no delivery taking place; to meet the requirements of multiple operating modes of the portable infusion device.

The Battery I is further coupled with a control unit and powers the control unit independently constituting a power supply circuit A, configured to ensure the infusion control of the portable infusion device by the control unit; the Battery II is further coupled with a driving unit and powers the driving unit independently constituting a power supply circuit B, configured to drive the drug infusion;

The power supply circuit A and the power supply circuit B are independent from each other; the Battery I and the Battery II have a clear division of labor: the Battery I powers the basic functions of the portable infusion device and charges Battery II, while the Battery II powers the high power functions of the portable infusion device. The Battery I is only responsible for small power supply and constant charging, so an easy-replaceable button battery is a good choice, while the Battery II is required to have a strong instantaneous discharging capacity to meet the needs of the high power function, making a supercapacitor with a super instantaneous discharging capacity a perfect choice.

Figure 2:
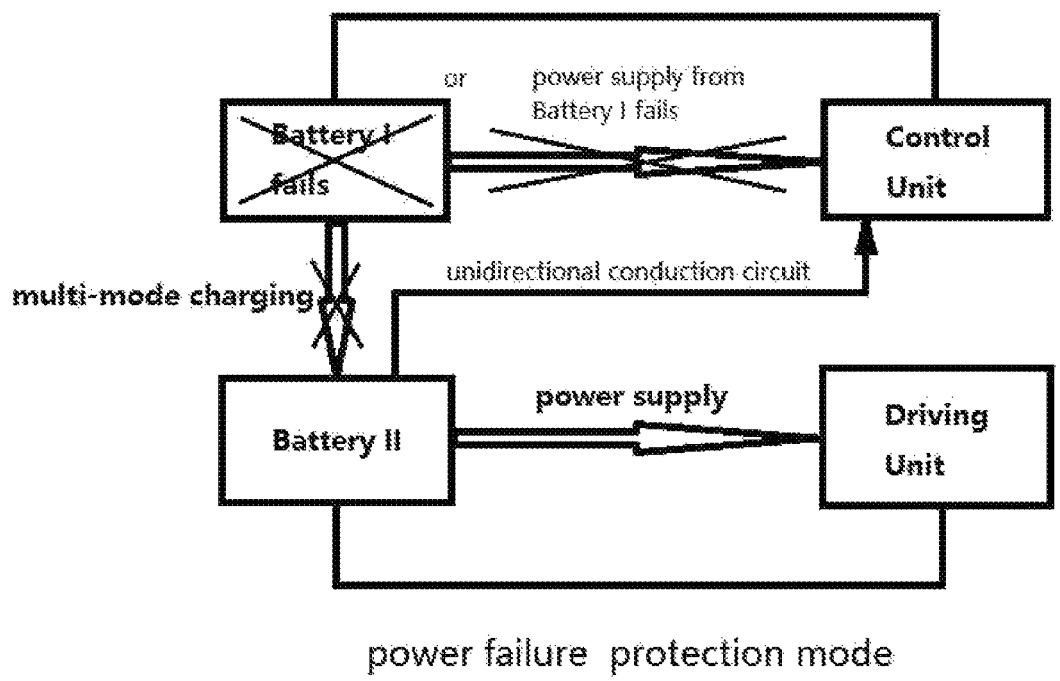
FIG. 2 illustrates a schematic of the multi-mode power supply system for a portable infusion device in the present invention in a power failure protection mode.

Referring to FIG. 2, an exemplary embodiment of the multi-mode power supply system for a portable infusion device in the present invention under a power failure protection mode is provided. As shown in the figure, when the Battery I suddenly fails or is disconnected from the power supply circuit A, the control unit cannot be powered by the power supply circuit A, so the multi-mode power supply system enters a power failure protection mode, under which the Battery II powers the control unit via the unidirectional conduction circuit, ensuring the normal operation of the control unit, so the portable infusion device can continue to operate normally in case the Battery I fails.

Figure 3:
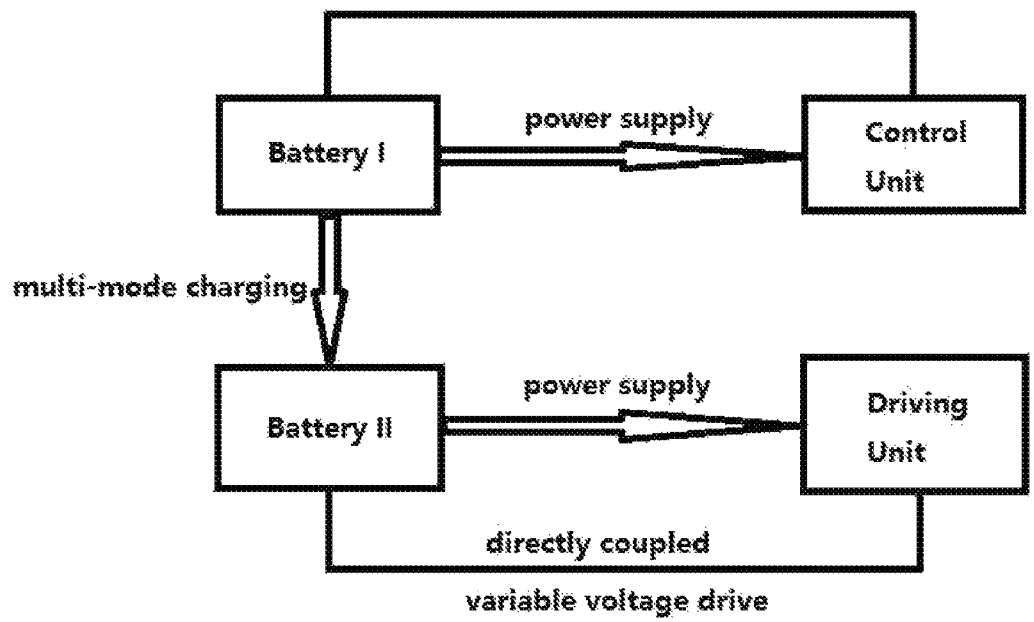
FIG. 3 illustrates a schematic of the multi-mode power supply system for a portable infusion device in the present invention when the Battery II powers the driving unit directly.

Referring to FIG. 3, an exemplary embodiment of the multi-mode power supply system for a portable infusion device in the present invention when the Battery II powers the driving unit directly is provided. As shown in the figure, the Battery II powers the driving unit directly, configured to implement a variable voltage drive for the system.

Figure 4:
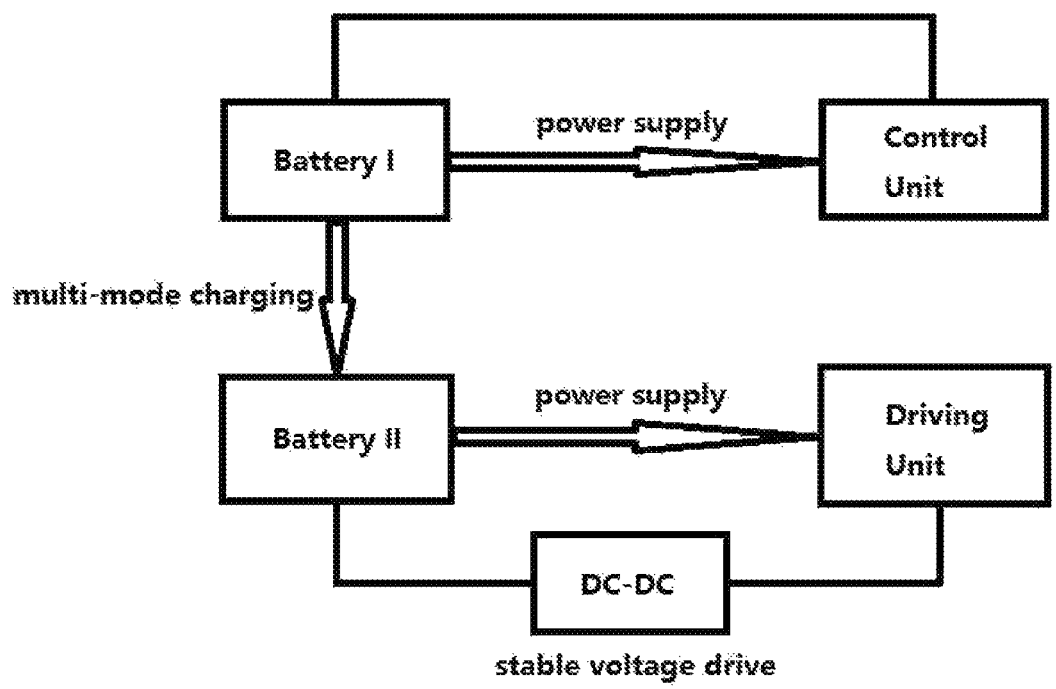
FIG. 4 illustrates a schematic of the multi-mode power supply system for a portable infusion device in the present invention when the Battery II is coupled with the driving unit via a DC-DC converter.

Referring to FIG. 4, an exemplary embodiment of the multi-mode power supply system for a portable infusion device in the present invention when the Battery II powers the driving unit via a DC-DC converter is provided. As shown in the figure, the Battery II is coupled with the driving unit via a DC-DC converter, configured to implement a stable voltage drive for the system.

Figure 5:
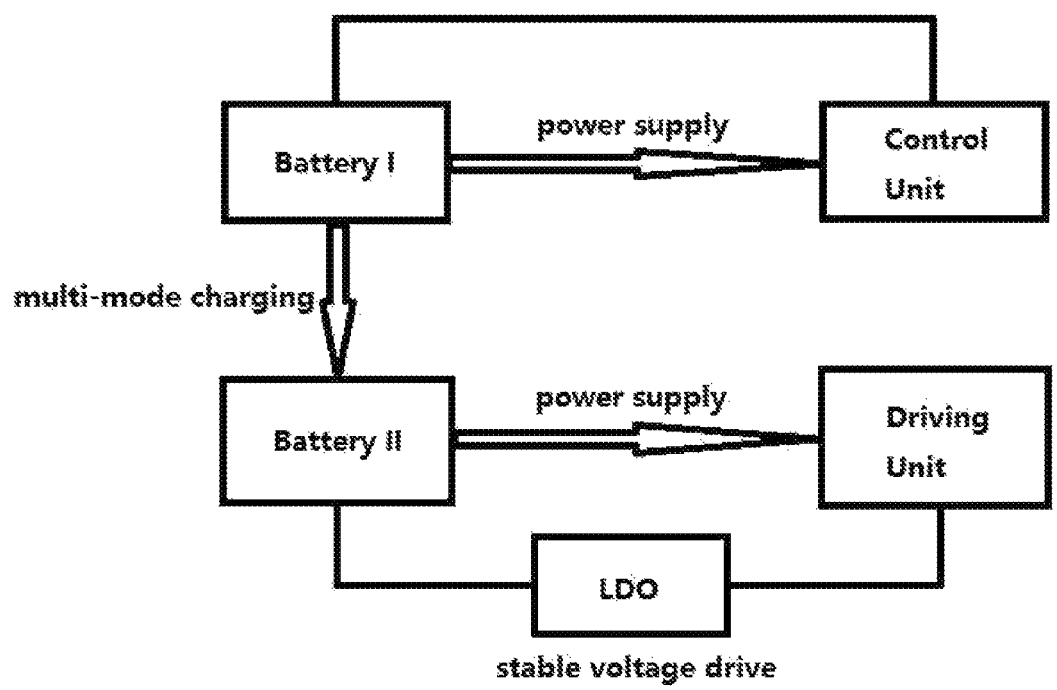
FIG. 5 illustrates a schematic of the multi-mode power supply system for a portable infusion device in the present invention when the Battery II is coupled with the driving unit via a LDO regulator.

Referring to FIG. 5, an exemplary embodiment of the multi-mode power supply system for a portable infusion device in the present invention when the Battery II powers the driving unit via a LDO regulator is provided. As shown in the figure, the Battery II is coupled with the driving unit via a LDO regulator, configured to implement a stable voltage drive for the system.

Figure 6:
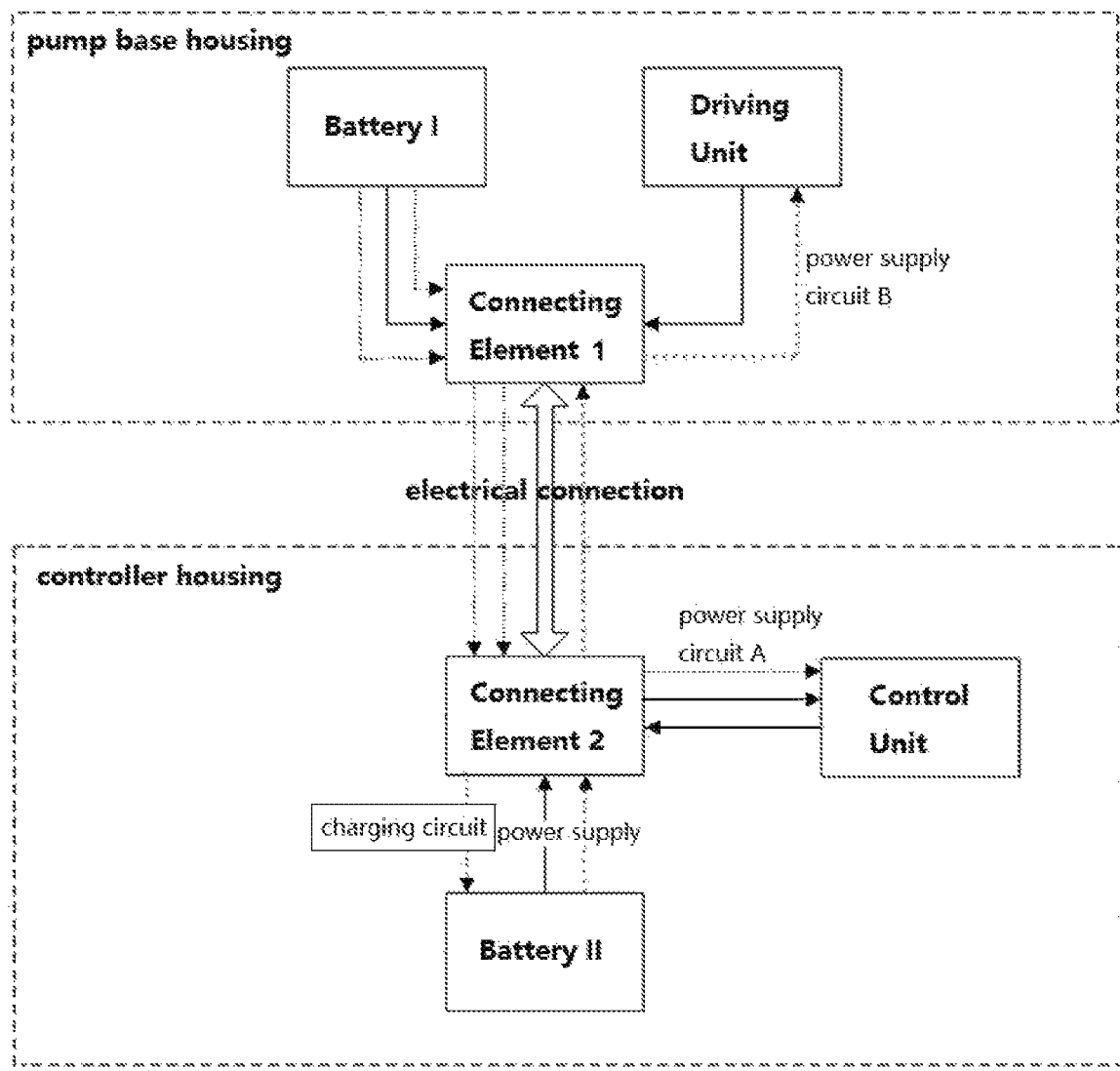
FIG. 6 illustrates a schematic of the multi-mode power supply system for a portable infusion device in the present invention when the Battery I and the driving unit are located in one housing, the Battery II and the control unit are located in the other housing, and the two housings are connected by connecting elements.

Referring to FIG. 6, also provided is an exemplary embodiment of the multi-mode power supply system for a portable infusion device in the present invention. In this embodiment, the Battery I, the driving unit and the connecting element 1 are located in the pump base housing; the Battery II, the control unit and the connecting element 2 are located in the controller housing; and the connecting element 1 is electrically connected with the connecting element 2, which implements the power supply from the Battery I to the control unit via the power supply circuit A, the power supply from the Battery II to the driving unit via the power supply circuit B, and the charging from the Battery I to the Battery II via the charging circuit.

What is claimed is:

1. A multi-mode power supply system for a portable infusion device, comprising:
A Battery I, a Battery II, the Battery I is coupled with the Battery II, the Battery I is further coupled with a control unit, the Battery II is further coupled with a driving unit;
wherein,
the Battery I is able to constantly charge the Battery II constituting a charging circuit, configured to maintain the voltage of the Battery II at a certain level;
the Battery I powers the control unit independently constituting a power supply circuit A, configured to ensure the infusion control of the portable infusion device by the control unit;
the Battery II powers the driving unit independently constituting a power supply circuit B, configured to drive the drug infusion;
the power supply circuit A and the power supply circuit B are independent from each other;
the charging circuit adopts one of multiple charging modes depending on different drug infusion conditions.

2. The multi-mode power supply system for a portable infusion device according to claim 1, wherein,
the multiple charging modes comprise:
a basal-rate slow charging mode, a bolus-dose fast charging mode and a background charging mode.

3. The multi-mode power supply system for a portable infusion device according to claim 1, wherein,
further comprises a unidirectional conduction circuit;
when the Battery I suddenly fails or is disconnected from the power supply circuit A, the multi-mode power supply system enters a power failure protection mode, under which the Battery II powers the control unit via the unidirectional conduction circuit.

4. The multi-mode power supply system for a portable infusion device according to claim 1, wherein,
further comprises a monitoring circuit;
the monitoring circuit is configured to monitor the voltage of the Battery II, controlling the Battery I to charge the Battery II when the voltage of the Battery II is below a predetermined amount, and suspending the charging when the voltage of the Battery II reaches another predetermined amount.

5. The multi-mode power supply system for a portable infusion device according to claim 1, wherein,
the Battery I is a button battery.

6. The multi-mode power supply system for a portable infusion device according to claim 1, wherein,
the Battery I is a wireless charging induction coil.

7. The multi-mode power supply system for a portable infusion device according to claim 1, wherein,
the Battery II is a supercapacitor.

8. The multi-mode power supply system for a portable infusion device according to claim 1, wherein,
the Battery I is a rechargeable battery.

9. The multi-mode power supply system for a portable infusion device according to claim 8, wherein,
the rechargeable battery is a lithium-ion battery or a NiMH battery.

10. The multi-mode power supply system for a portable infusion device according to claim 1, wherein,
further comprises a detecting circuit;
the detecting circuit is configured to monitor the operating state of the driving unit in real time via detecting the voltage change of the Battery II caused by a single time infusion.

11. The multi-mode power supply system for a portable infusion device according to claim 1, wherein,
the Battery II powers the driving unit directly, configured to implement a variable voltage drive.

12. The multi-mode power supply system for a portable infusion device according to claim 1, wherein,
the Battery II powers the driving unit via a DC-DC converter, configured to implement a stable voltage drive.

13. The multi-mode power supply system for a portable infusion device according to claim 1, wherein,
the Battery II powers the driving unit via a LDO regulator, configured to implement a stable voltage drive.

14. The multi-mode power supply system for a portable infusion device according to claim 1, wherein,
further comprises a connecting element or connecting elements;
any two of the Battery I, the Battery II, the driving unit and the control unit are located in one housing, and the other two are located in the other housing;
regardless of any particular combination of these four components in the two housings, the coupling of the Battery I with the control unit and the Battery II with the driving unit are both implemented directly by a connecting element or connecting elements,
the number of the connecting element or connecting elements can be one or more.

15. The multi-mode power supply system for a portable infusion device according to claim 1, wherein,
the portable infusion device is a patch pump.

* * * * *